United States Patent
Hand et al.

(10) Patent No.: US 6,526,610 B1
(45) Date of Patent: Mar. 4, 2003

(54) PRONING BED

(75) Inventors: Barry D. Hand, Mt. Pleasant, SC (US); Dana H. Delk, North Charleston, SC (US); Jack J. Brooks, Folly Beach, SC (US); Steven J. Doehler, Charleston, SC (US)

(73) Assignee: Hill-Rom Services, Inc., Wilmington, DE (US)

(*) Notice: Subject to any disclaimer, the term of this patent is extended or adjusted under 35 U.S.C. 154(b) by 0 days.

(21) Appl. No.: 09/701,624

(22) PCT Filed: Jun. 25, 1999

(86) PCT No.: PCT/US99/14525

§ 371 (c)(1),
(2), (4) Date: Dec. 1, 2000

(87) PCT Pub. No.: WO00/00152

PCT Pub. Date: Jan. 6, 2000

Related U.S. Application Data

(60) Provisional application No. 06/090,847, filed on Jun. 26, 1998.

(51) Int. Cl.[7] ................................................. A61G 7/057
(52) U.S. Cl. .................. 5/607; 5/609; 5/600; 5/81.1 R; 5/89.1; 5/658; 5/503.1
(58) Field of Search ............................... 5/600, 607, 609, 5/620, 621, 626, 430, 503.1, 658, 81.1 R, 86.1, 89.1

(56) References Cited

U.S. PATENT DOCUMENTS

| | | |
|---|---|---|
| 1,573,571 A | 2/1926 | Pohl |
| 1,667,982 A | 5/1928 | Pearson |
| 1,799,692 A | 4/1931 | Knott |
| 2,076,675 A | 4/1937 | Sharp |
| 2,239,821 A | 4/1941 | Knox |
| 2,311,542 A | 2/1943 | Holme |
| 2,417,378 A | 3/1947 | Robinson |
| 2,499,101 A | 2/1950 | Kluglein |
| 2,607,103 A | 8/1952 | Davidson |
| 2,613,371 A | 10/1952 | Keyes, Jr. |
| 2,639,206 A | 5/1953 | Butler |
| 2,667,169 A | 1/1954 | Kambourakis |
| 2,673,987 A * | 4/1954 | Upshaw et al. ............... 269/61 |
| 2,803,022 A | 8/1957 | Wynkoop |
| 2,880,720 A | 4/1959 | Houghtaling |
| 2,902,701 A | 9/1959 | Driskill |
| 3,049,726 A * | 8/1962 | Getz ............................. 5/86.1 |
| 3,110,912 A | 11/1963 | Propst |
| 3,200,416 A | 8/1965 | Warrick |
| 3,226,734 A | 1/1966 | Coventon |
| 3,238,539 A * | 3/1966 | Koch ............................. 5/430 |
| 3,286,707 A | 11/1966 | Shafer |

(List continued on next page.)

FOREIGN PATENT DOCUMENTS

| | | |
|---|---|---|
| EP | 0 569 308 A1 | 5/1993 |
| FR | 2.034.679 | 12/1970 |
| FR | 2 247 194 | 5/1975 |
| FR | 2 549 366 | 1/1985 |
| FR | 2 585 240 | 1/1987 |
| TW | 77886 | 11/1975 |
| WO | WO 93/05745 | 9/1992 |

Primary Examiner—Michael F. Trettel
(74) Attorney, Agent, or Firm—Bose McKinney & Evans LLP

(57) ABSTRACT

A bed (10) includes a base (12), and a support assembly (22) coupled to the base (12). The support assembly includes first and second support arms (42, 44) located above the base (12). The bed (10) also includes a plurality of latch mechanisms (70, 72, 74) coupled to the first and second support arms (42, 44), and a patient support surface (50) configured to be coupled to the first and second support arms (42, 44) by the plurality of latch mechanisms (70, 72, 74). The patient support surface (50) is removable from the first and second support arms (42, 44) to permit transfer of a patient to and from the bed (10) on the patient support surface (50).

45 Claims, 9 Drawing Sheets

U.S. PATENT DOCUMENTS

| | | | |
|---|---|---|---|
| 3,302,218 A | * | 2/1967 | Stryker ...................... 5/507.1 |
| 3,344,445 A | | 10/1967 | Crawford |
| 3,388,700 A | | 6/1968 | Mountz |
| 3,434,165 A | | 3/1969 | Keane |
| 3,451,070 A | * | 6/1969 | Danielson ...................... 5/83.1 |
| 3,499,529 A | | 3/1970 | Katzfey et al. |
| 3,584,321 A | | 6/1971 | Buchanan |
| 3,653,079 A | | 4/1972 | Bourgraf et al. |
| 3,658,052 A | | 4/1972 | Alter |
| 3,737,924 A | | 6/1973 | Davis |
| 3,739,406 A | | 6/1973 | Koetter |
| 3,748,666 A | | 7/1973 | Seng |
| 3,752,153 A | | 8/1973 | Copeland |
| 3,765,406 A | | 10/1973 | Toole et al. |
| 3,783,863 A | | 1/1974 | Kliever |
| 3,814,414 A | | 6/1974 | Chapa |
| 3,820,176 A | | 6/1974 | Feiertag |
| 3,827,089 A | | 8/1974 | Grow |
| 3,828,377 A | | 8/1974 | Eary, Sr. |
| 3,832,742 A | | 9/1974 | Stryker |
| 3,851,644 A | | 12/1974 | Slagle |
| 3,874,010 A | | 4/1975 | Geary |
| 3,884,225 A | | 5/1975 | Witter |
| 3,902,204 A | * | 9/1975 | Lee ............................... 5/86.1 |
| 3,905,591 A | | 9/1975 | Schorr et al. |
| 3,940,808 A | * | 3/1976 | Petrini ...................... 5/81.1 RP |
| 3,941,365 A | | 3/1976 | Frymoyer |
| 4,054,960 A | | 10/1977 | Pettit et al. |
| 4,080,673 A | | 3/1978 | Weisler |
| 4,084,274 A | | 4/1978 | Willis et al. |
| 4,109,329 A | | 8/1978 | Tupper |
| 4,152,795 A | | 5/1979 | Rodosta et al. |
| 4,156,815 A | | 5/1979 | Hogan |
| 4,175,550 A | | 11/1979 | Leininger et al. |
| 4,183,110 A | | 1/1980 | Kidd et al. |
| 4,244,358 A | | 1/1981 | Pyers |
| 4,274,167 A | | 6/1981 | Immel |
| 4,277,857 A | | 7/1981 | Svehaug |
| 4,356,577 A | | 11/1982 | Taylor et al. |
| 4,384,378 A | | 5/1983 | Getz et al. |
| 4,395,786 A | | 8/1983 | Casey et al. |
| 4,432,353 A | | 2/1984 | Vrzalik |
| 4,490,867 A | | 1/1985 | Gabrielson |
| 4,572,493 A | | 2/1986 | Hubert |
| 4,578,833 A | | 4/1986 | Vrzalik |
| 4,584,989 A | | 4/1986 | Stith |
| 4,586,492 A | | 5/1986 | Manahan |
| 4,619,270 A | | 10/1986 | Margolis et al. |
| 4,655,206 A | | 4/1987 | Moody |
| 4,658,450 A | | 4/1987 | Thompson |
| 4,763,643 A | | 8/1988 | Vrzalik |
| 4,769,584 A | | 9/1988 | Irigoyen et al. |
| 4,827,541 A | | 5/1989 | Vollman et al. |
| 4,841,585 A | | 6/1989 | Masuzawa |
| 4,852,193 A | | 8/1989 | Alsip et al. |
| 4,856,128 A | | 8/1989 | Alsip et al. |
| 4,866,796 A | | 9/1989 | Robinson et al. |
| 4,868,937 A | | 9/1989 | Connolly |
| 4,872,657 A | | 10/1989 | Lussi |
| 4,895,173 A | | 1/1990 | Brault et al. |
| 4,912,754 A | | 3/1990 | Van Steenburg |
| 4,920,589 A | | 5/1990 | LaVelle et al. |
| 4,924,537 A | | 5/1990 | Alsip et al. |
| 4,939,801 A | | 7/1990 | Schaal et al. |
| 4,941,221 A | | 7/1990 | Kanzler |
| 4,944,054 A | | 7/1990 | Bossert |
| 4,947,496 A | | 8/1990 | Connolly |
| 4,958,817 A | | 9/1990 | Heller et al. |
| 4,960,271 A | | 10/1990 | Sebring |
| 4,987,622 A | | 1/1991 | Shockey |
| 4,988,062 A | * | 1/1991 | London ............... 128/DIG. 26 |
| 5,005,233 A | | 4/1991 | Toivio et al. |
| 5,018,712 A | | 5/1991 | Schaefer |
| 5,020,170 A | | 6/1991 | Ruf |
| 5,023,968 A | | 6/1991 | Diehl et al. |
| 5,048,071 A | | 9/1991 | Van Steenburg |
| 5,060,324 A | | 10/1991 | Marinberg et al. |
| 5,088,706 A | | 2/1992 | Jackson |
| 5,092,007 A | | 3/1992 | Hasty |
| 5,103,511 A | | 4/1992 | Sequin |
| 5,131,103 A | | 7/1992 | Thomas et al. |
| 5,131,105 A | | 7/1992 | Harrawood et al. |
| 5,131,106 A | * | 7/1992 | Jackson ........................ 5/607 |
| 5,148,815 A | | 9/1992 | Britton |
| 5,152,024 A | | 10/1992 | Chrones et al. |
| 5,181,288 A | | 1/1993 | Heaton et al. |
| 5,208,928 A | | 5/1993 | Kuck et al. |
| 5,230,112 A | | 7/1993 | Harrawood et al. |
| 5,274,862 A | | 1/1994 | Palmer, Jr. et al. |
| 5,299,334 A | | 4/1994 | Gonzalez |
| 5,319,817 A | | 6/1994 | Hay et al. |
| 5,334,186 A | * | 8/1994 | Alexander ........... 128/DIG. 15 |
| 5,336,179 A | * | 8/1994 | Ryan ................... 128/DIG. 26 |
| 5,404,603 A | | 4/1995 | Fukai et al. |
| 5,412,823 A | | 5/1995 | Sitta |
| 5,418,990 A | | 5/1995 | Risasen |
| 5,427,338 A | * | 6/1995 | Garrett et al. ......... 128/DIG. 6 |
| 5,435,323 A | | 7/1995 | Rudy |
| 5,502,853 A | | 4/1996 | Singleton et al. |
| 5,515,561 A | | 5/1996 | Suggitt et al. |
| 5,515,869 A | | 5/1996 | Powell et al. |
| 5,621,932 A | | 4/1997 | Strachan |
| 5,664,270 A | | 9/1997 | Bell et al. |
| 5,699,568 A | | 12/1997 | Couldridge |
| 6,065,165 A | | 5/2000 | Delk et al. |
| 6,108,838 A | | 8/2000 | Connolly et al. |
| 6,112,349 A | | 9/2000 | Connolly |
| 6,375,017 B1 | * | 4/2002 | Schattner et al. ............. 211/70 |

* cited by examiner

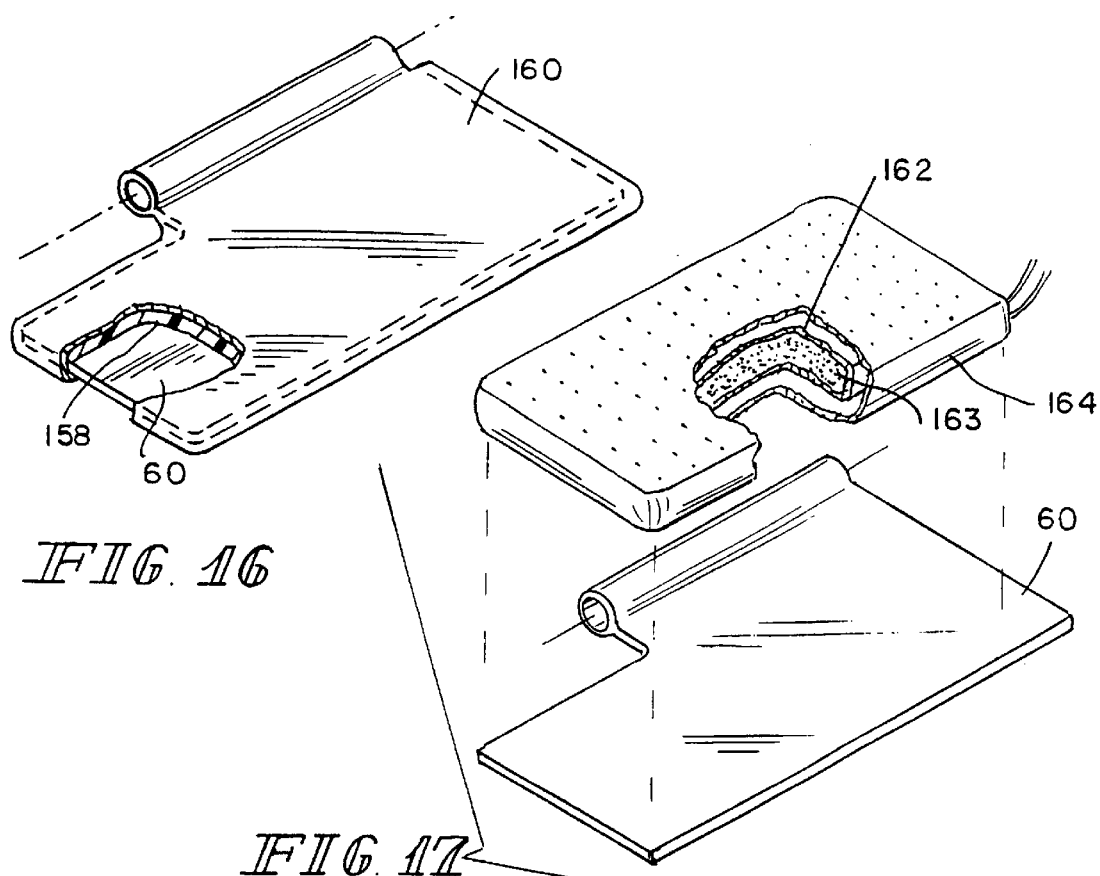
FIG. 16
FIG. 17
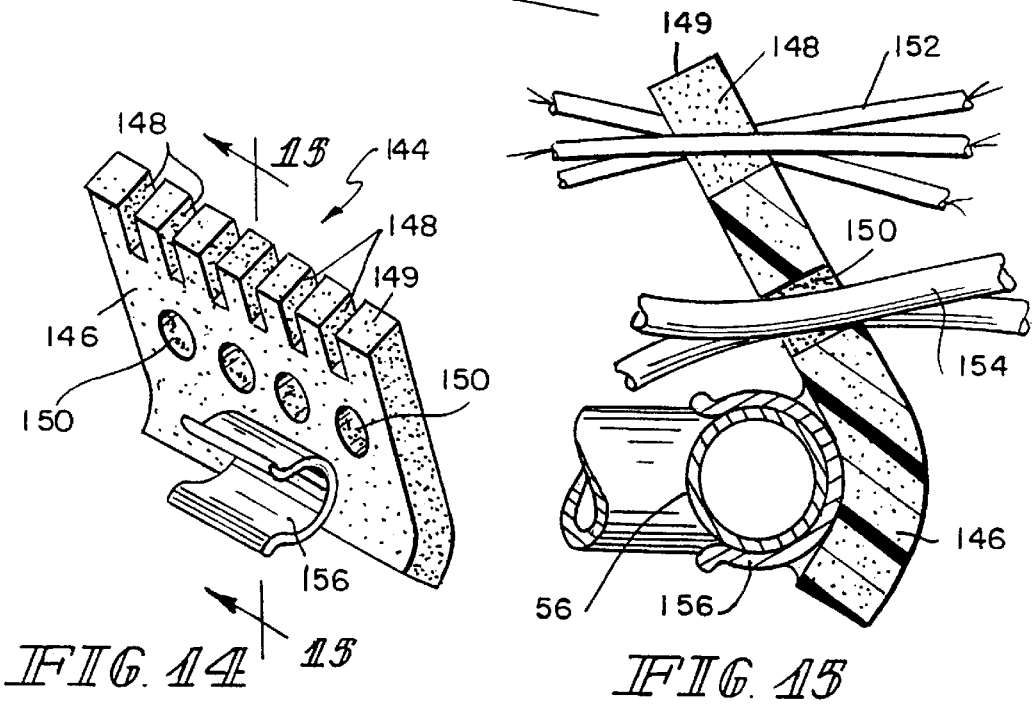
FIG. 14
FIG. 15

PRONING BED

This application claims the benefit of No. 60/090,847, filed Jun. 26, 1998.

BACKGROUND AND SUMMARY OF THE INVENTION

The present invention relates to a hospital bed. More particularly, the present invention relates to a proning bed which permits rotation of a patient supported on a patient support surface of the bed.

A bed of the present invention illustratively includes a base, and a support assembly coupled to the base. The support assembly includes first and second support arms located above the base. The apparatus also includes a plurality of latch mechanisms coupled to the first and second support arms, and a patient support surface configured to be coupled to the first and second support arms by the plurality of latch mechanisms. The patient support surface is removable from the first and second support arms to permit transfer of a patient to and from the bed on the patient support surface.

In an illustrated embodiment, the support assembly is coupled to a first end of the base. The support assembly includes a rotatable drive mechanism coupled to the first and second support arms for rotating the first and second arms about a longitudinal axis. The first and second support arms may be cantilevered from the support assembly or coupled to a support located at the end of the second base.

A proning surface is configured to be coupled to the first and second support arms. The proning surface is configured to support the patient in a prone position when the patient support assembly is rotated 180° about its longitudinal axis by the drive mechanism. In an illustrated embodiment, a plurality of siderails is coupled to the first and second support arms. The siderails each include a portion which is movable over the patient support surface to form a portion of the proning surface.

The illustrated patient support surface includes an outer frame configured to be coupled to the plurality of latch mechanisms to secure the patient support surface to the first and second support arms. The patient support surface also includes a plurality of panels coupled to the outer frame. The panels illustratively include notched portions configured to define handles on the patient support surface. The plurality of panels is pivotably coupled to the outer frame.

The illustrated patient support surface further includes at least one hinge to permit articulation of the patient support surface. The patient support surface includes at least one locking member configured to block pivotal movement of the hinge to hold the patient support surface in a generally planar orientation. The support assembly includes an actuator for selectively releasing the locking member to permit articulation of the patient support surface. In an illustrated embodiment, a latching mechanism is configured to engage each locking member. The actuator is configured to move the latching mechanism relative to the first and second support arms to expose the hinge and permit articulation of the patient support surface.

The illustrated embodiment of the present invention includes a transfer surface coupled to the base. The transfer surface is movable from a lowered position to an elevated position located adjacent the first and second support arms when the patient support surface is coupled to and removed from the first and second support arms. In one embodiment, the transfer surface is configured to engage a portion of the plurality of latch mechanisms as the transfer surface is moved to the elevated position to open the latch mechanisms for receiving the patient support surface.

A line management apparatus of the present invention is configured to be coupled to a patient support surface for routing medical lines and hoses. The apparatus includes a body portion having a top edge. The body portion is formed to include a plurality of notches opening along the top edge to receive the lines and hoses and a plurality of apertures located below the notches for receiving additional lines and hoses. A coupler is coupled to the body portion adjacent to the plurality of apertures. The coupler is configured to connect the body portion to the patient support surface Additional features of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying drawings in which:

FIG. 14 is a perspective view of a line management apparatus of the present invention configured to be coupled to the outer frame of the patient support surface;

FIG. 15 is a sectional view taken along lines 15—15 of FIG. 14 with the line management apparatus installed on the outer frame of the patient support surface;

FIGS. 16 and 17 illustrate cushions configured to be located over the panels of the patient support surface;

DETAILED DESCRIPTION OF THE DRAWINGS

Figure 1:
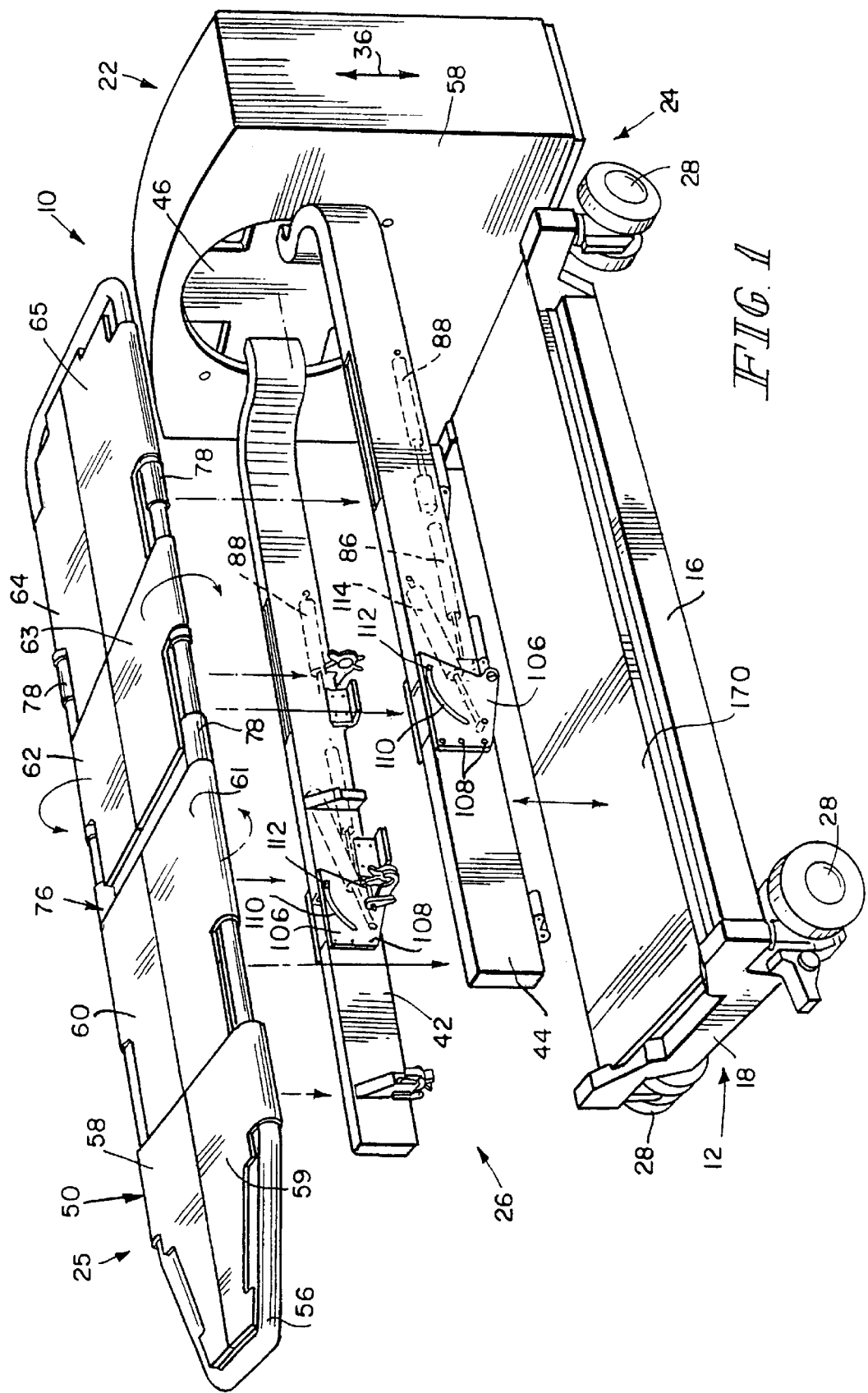
FIG. 1 is an exploded perspective view of a proning bed of the present invention including a patient support surface spaced apart from first and second support arms which are coupled to a rotating support assembly.

Referring now to the drawings, FIG. 1 illustrates a bed 10 having a base 12 which includes opposite side members 14 and 16 and cross members 18 and 20 extending between side members 14 and 16. A support assembly 22 is located at a foot end 24 of bed 10. Support assembly 22 supports a patient support assembly 26 in a cantilevered fashion. Therefore, the head end 25 of bed 10 is open to facilitate access to the patient (not shown). It is understood that in another embodiment of the present invention a support is coupled to the head end of the base 12 for supporting the head end of the patient support assembly 26. Therefore, the present invention is not limited to a cantilevered design.

Support assembly 22 is coupled to base 12. Base 12 is supported by casters 28 which are illustratively lockable. The support assembly 22 is movable up and down in the direction of double-headed arrow 36 to raise and lower the height of patient support assembly 26. Support assembly 22 can rotate the patient support assembly 26 about its longitudinal axis 38 as indicated by double-headed arrow 40. Support assembly 22 can rotate the patient support assembly 26 in either direction a full 360°. In other words, the patient can be rotated 180° to prone the patient to aid with respiratory disorders such as ARDS, or in order to perform surgical procedures or to permit the patient to lie face down on the support surface. The present invention permits full 180° rotation of a patient located on a patient support surface while providing spinal stability for spinal trauma patients. A proning surface (not shown in FIGS. 1 and 2) is attached to the patient support assembly 26 before the patient support assembly 26 is rotated.

Patient support assembly 26 includes a pair of horizontally extending support arms 42 and 44 which are coupled to a cruciform-shaped plate 46 of support assembly 22. In the illustrated embodiment, the arms 42 and 44 extend away from support assembly 22 in a cantilevered fashion. A patient support surface 50 is coupled between arms 42 and 44 as discussed below.

Cruciform 46 is coupled to a rotatable, annular rack which is held in place on a front surface 58 of support assembly 22 by rotatable bearings which are also coupled to front surface 58. Cruciform 46 includes four arms which are each secured to the annular rack. A motor and gear are located on support assembly 22. The gear engages the annular rack to rotate the annular rack relative to the front surface 58. Therefore, the support arms 42 and 44 coupled to the cruciform also rotate in the direction of double-headed arrow 40 in FIG. 2. Details of the support assembly 22 are described in PCT International Publication No. WO 99/07320 which is incorporated herein by reference.

Patient support surface 50 includes an outer frame 56 and the plurality of panels 58–65 which are pivotably coupled to the outer support frame 56 by pivot connections 66. In the illustrated embodiment, the panels 58–65 are all pivotable upwardly or downwardly about opposite sides of outer frame 56. This pivotable movement of panels 58–65 provides access to the patient when in the prone position. Portions of panels 58–65 are spaced apart from outer frame 56 to provide hand access for gripping the patient support surface 50 during transport. In other words, apertures or notches in panels 58–65 define grip locations 68 for the patient support surface 50.

Figure 3:
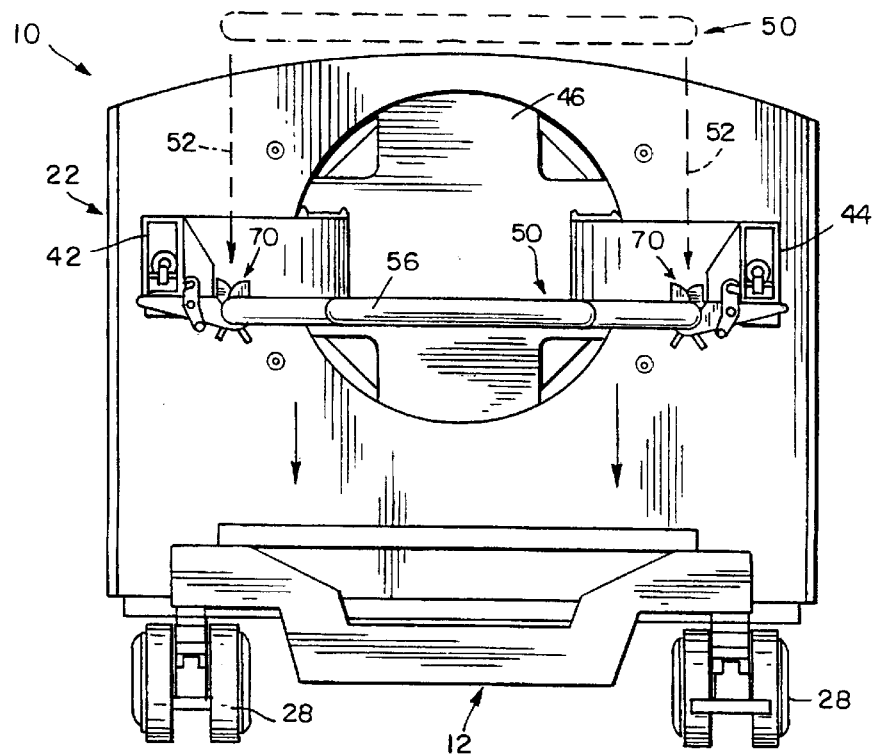
FIG. 3 is an end view of the bed of FIGS. 1 and 2 illustrating coupling of the patient support surface to the first and second support arms by latch mechanisms.

The patient support surface 50 is designed for use in the field at an injury location for transporting a patient in the manner of a backboard or stretcher. The support surface 50 is then loaded into the bed 10 without having to move the patient off of the surface 50. Bed 10 includes latching mechanisms 70, 72, and 74 for a head panel, seat panel, and leg panel, respectively, of the patient support surface 50. When the patient support surface 50 is brought to the bed 10, it is lowered between the side arms 42 and 44 as shown by arrows 52 in FIG. 3 and automatically latched by the latching mechanisms 70, 72, and 74 which engage the outer frame member 56 as discussed below.

Figure 5:
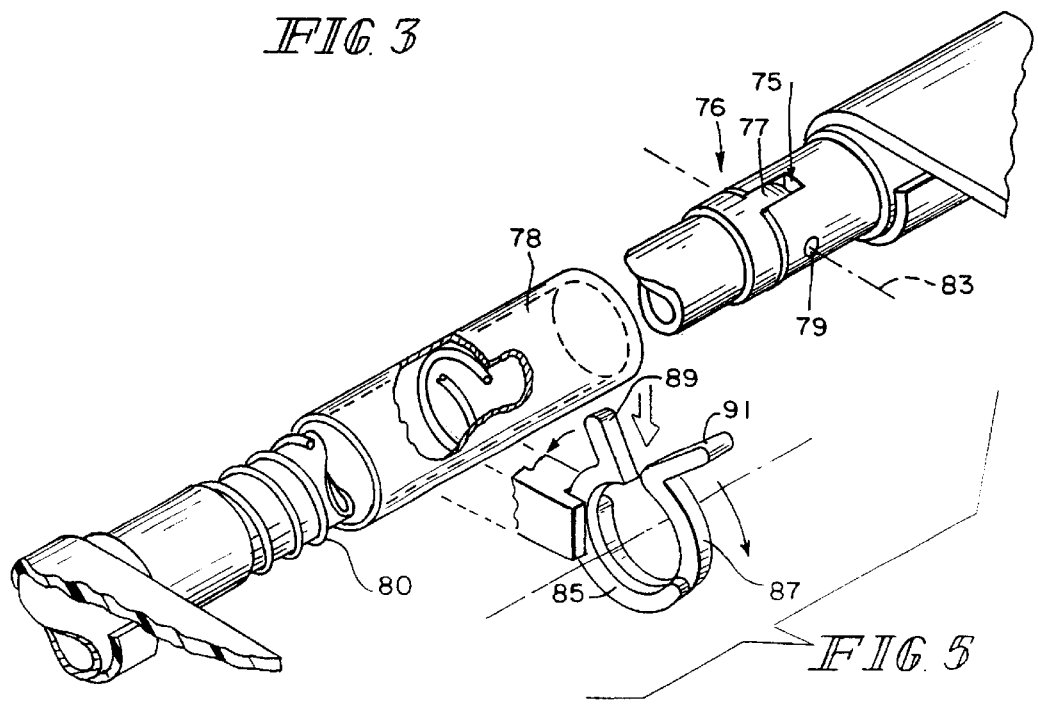
FIG. 5 is an exploded perspective view illustrating details of a hinge of the patient support surface, a locking cylinder movable on an outer frame of the patient support surface for blocking articulation of the patient support surface, and the latch mechanism.
Figures 4, 6:
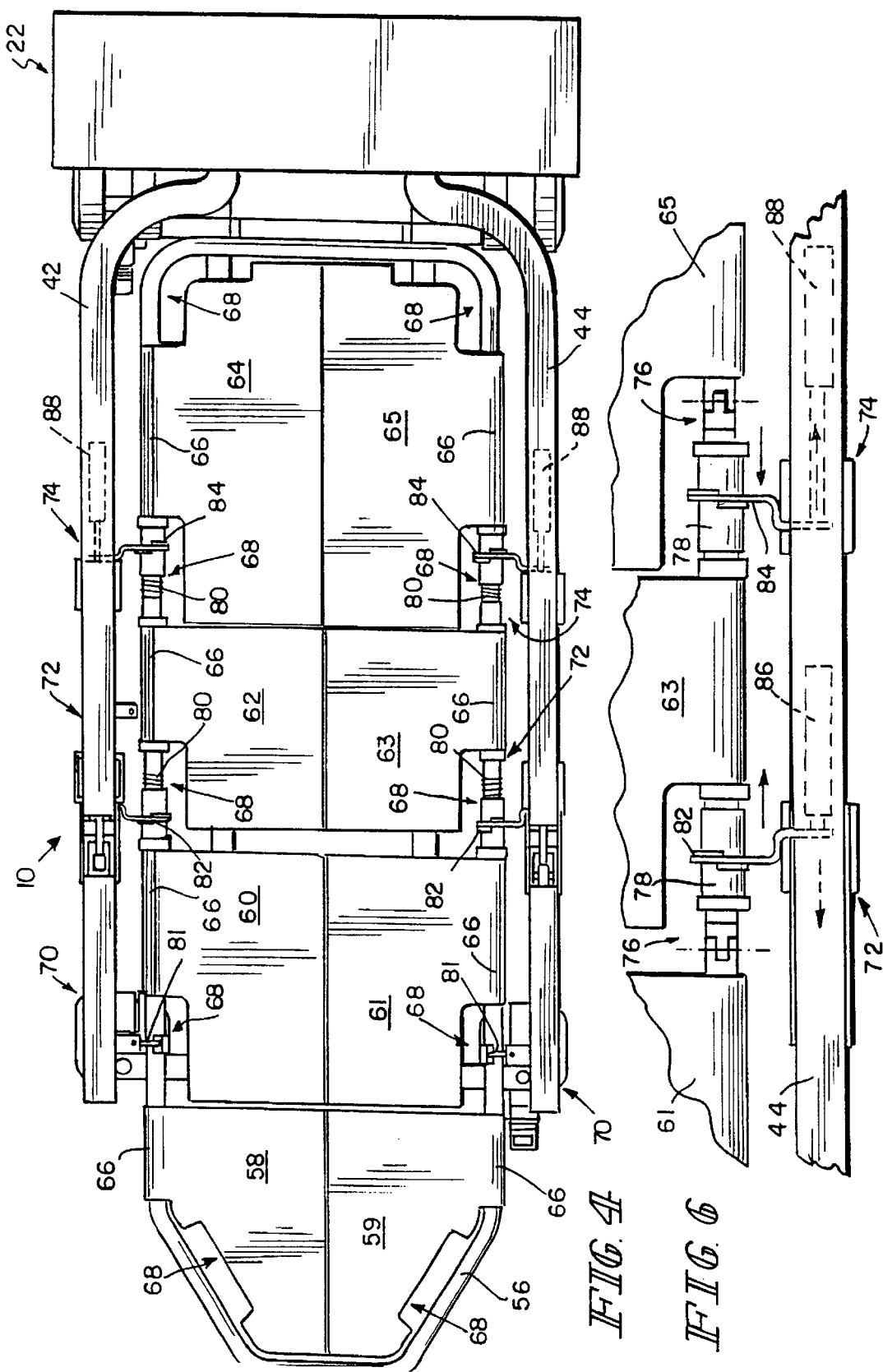
FIG. 4 is a top plan view of the bed of FIG. 2.
FIG. 6 is a partial view of the bed of FIG. 4 illustrating movement of first and second latch mechanisms to move the locking cylinders away from the hinges to permit articulation of the patient support surface.

The patient support surface 50 includes hinge connections 76 between the head section which includes panels 58–61 and the seat section which includes panels 62 and 63. Hinge connections 76 are also provided between panels 62 and 63 and the leg section which includes panels 64 and 65. The hinge connections 76 are best illustrated in FIG. 5. The hinge connections 76 are covered with slidable locking cylinders 78 during transport to prevent pivoting movement of the patient support surface 50. The cylinders 78 are shown in a locked position in FIGS. 1, 2 and 4. Illustratively, the locking cylinders 78 are biased to the closed position by a springs 80. FIGS. 5 and 6 illustrate cylinders 78 in open positions so that hinges 76 are exposed to permit articulation between adjacent head, seat and foot sections of patient support surface 50.

Figure 10:
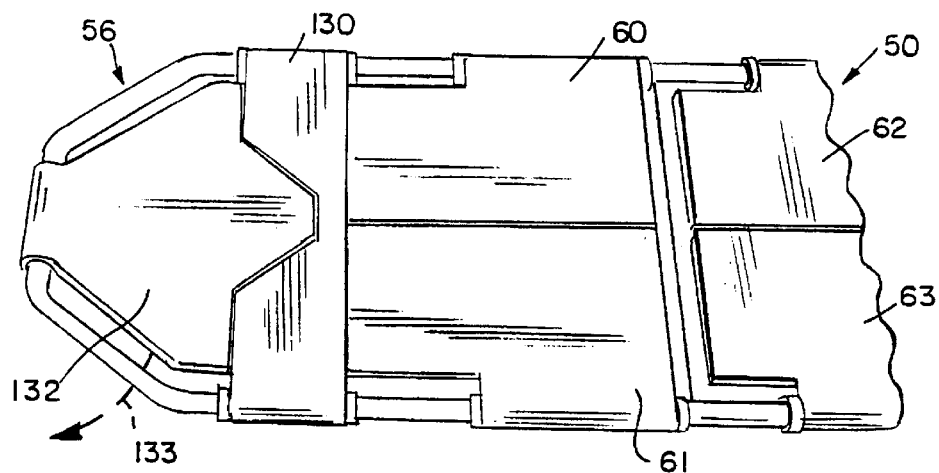
FIG. 10 is a perspective view of another patient support surface of the present invention.

Patient support surface 50 is loaded into the bed 10 with cylinders 78 in the locked position. As shown in FIG. 10, latches 81 of latch mechanism 70 engage a portion of the outer frame 56. Latches 82 of latch mechanisms 72 engage the cylinders 78 between head and seat sections of the patient support 50. Latches 84 of latch mechanisms 74 engage the cylinders 78 between the seat section and foot sections of patient support surface 50. Hydraulic cylinders 86 and 88 are coupled to latch mechanisms 72 and 74, respectively, as best shown in FIG. 6. Cylinders 86 and 88 are located within frame members 42 and 44 on each side of the bed 10. Cylinders 86 are actuated to move the latches 82 toward foot end 24 of bed 10. Movement of latches 82 causes movement of locking cylinders 78 away from the hinges 76 located between the head section and the seat section of patient support surface 50 to permit articulation of the head section of the patient support surface 50. Similarly, cylinders 88 are actuatable to move latches 84 toward the head end 25 of bed 10. Such a movement causes the locking cylinders 78 to move toward head end 25 and expose hinges 76 between the seat section and the foot section of the patient support surface 50 to permit articulation of the foot section. Cylinders 86 and 88 can be actuated automatically upon installation of the patient support surface 50 into the bed 10. Otherwise, the cylinders 86 and 88 are actuated only when articulation of the patient support surface 50 is initiated. In this instance, the cylinders 86 and 88 keep the locking cylinders 78 over the hinges 76 until articulation is initiated.

Figure 7:
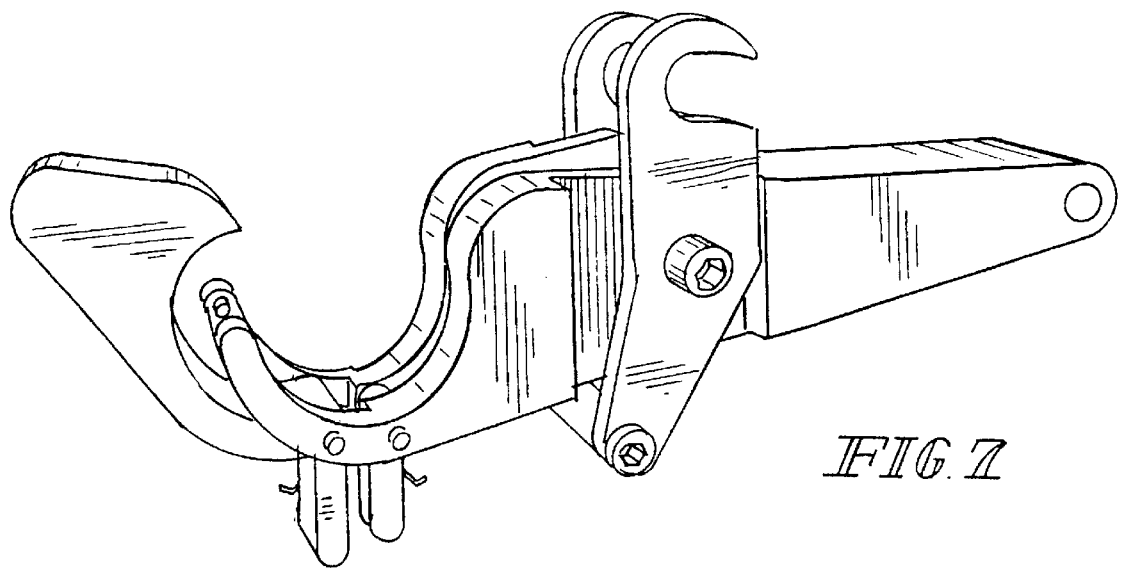
FIGS. 7 and 8 illustrate additional embodiments of latching mechanisms.
Figure 8:
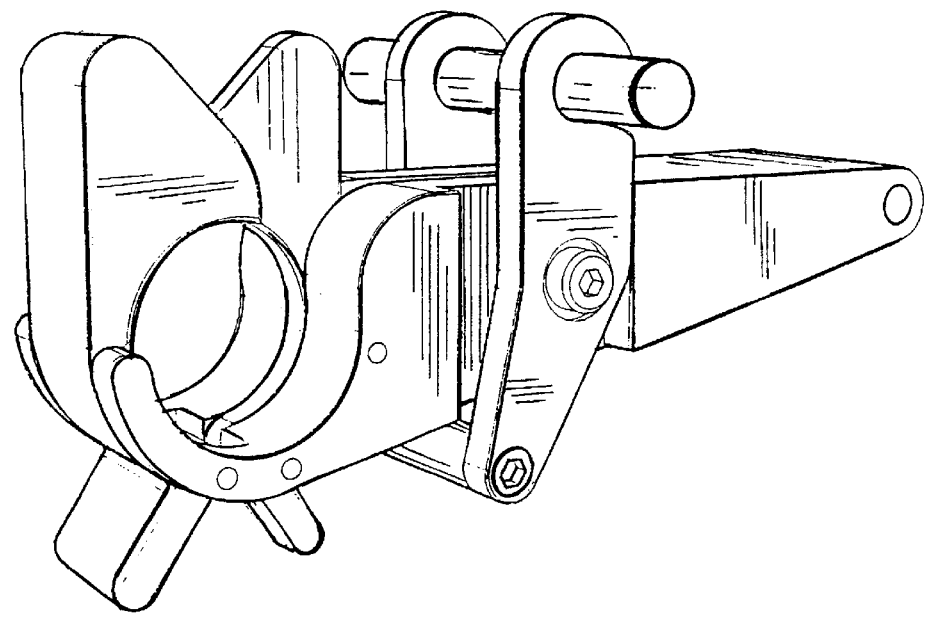

Further details of the hinges 76 are illustrated in FIG. 5. Hinge includes a slot 75 formed in a first portion of frame 56 and a tab 77 formed on a second portion of frame 56. A pivot pin 79 extends through the slot 75 and tab 77 so that the hinge 76 pivots about axis 83. The latches 81, 82 and 84 include first and second latch portions 85 and 87 as shown in FIG. 5. Latch portions 85 and 87 include lead-in ramp surfaces 89 and 91, respectively, so that the latches are automatically opened during insertion of the patient support surface 50. In another embodiment, the latches 81, 82 and 84 are opened by upward movement of the transfer surface 170. Other configurations of the latches 81, 82 and 84 are illustrated in FIGS. 7 and 8.

Figure 2:
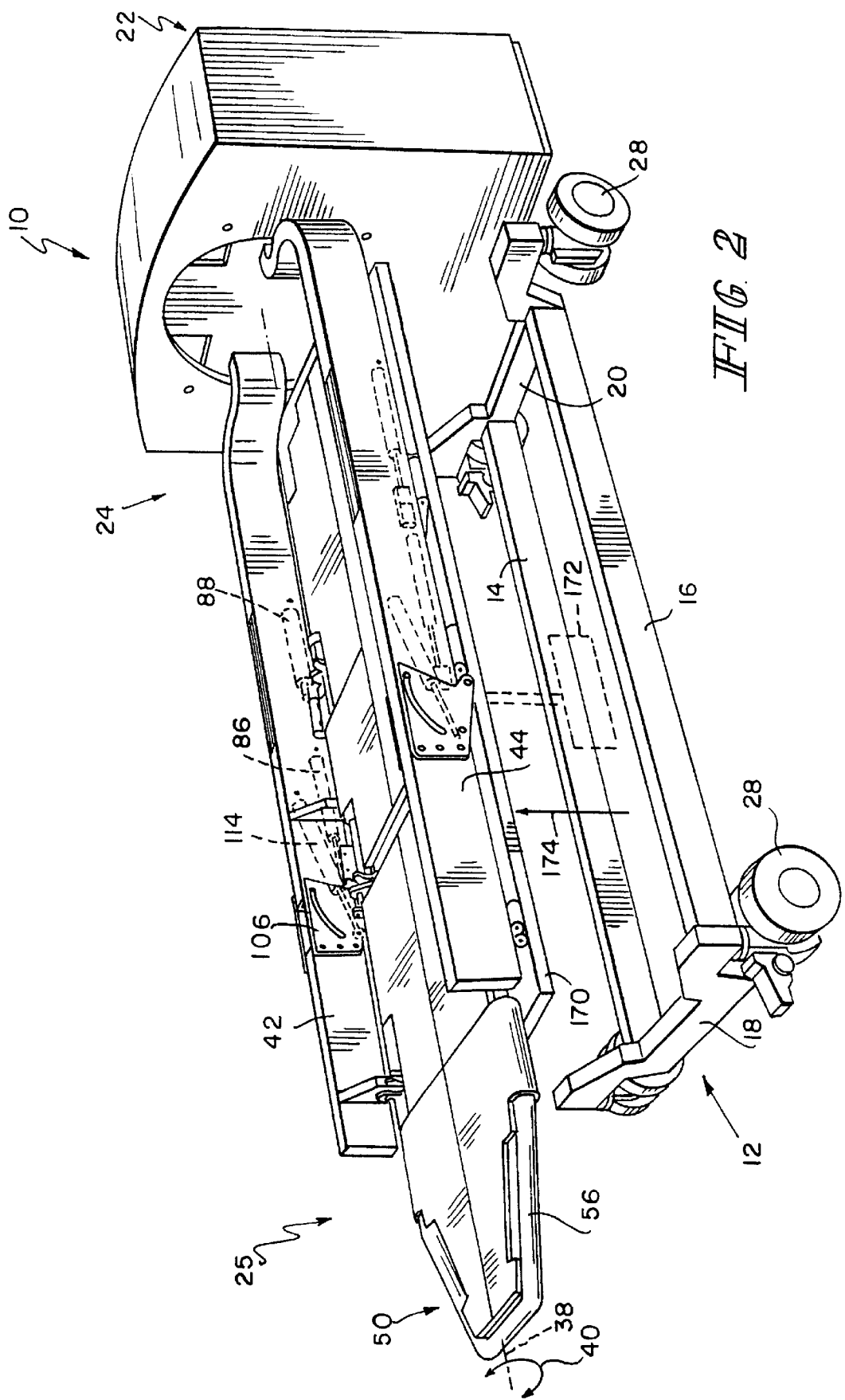
FIG. 2 is a perspective view similar to FIG. 1 in which the patient support surface has been coupled to the first and second support arms.
Figure 9:
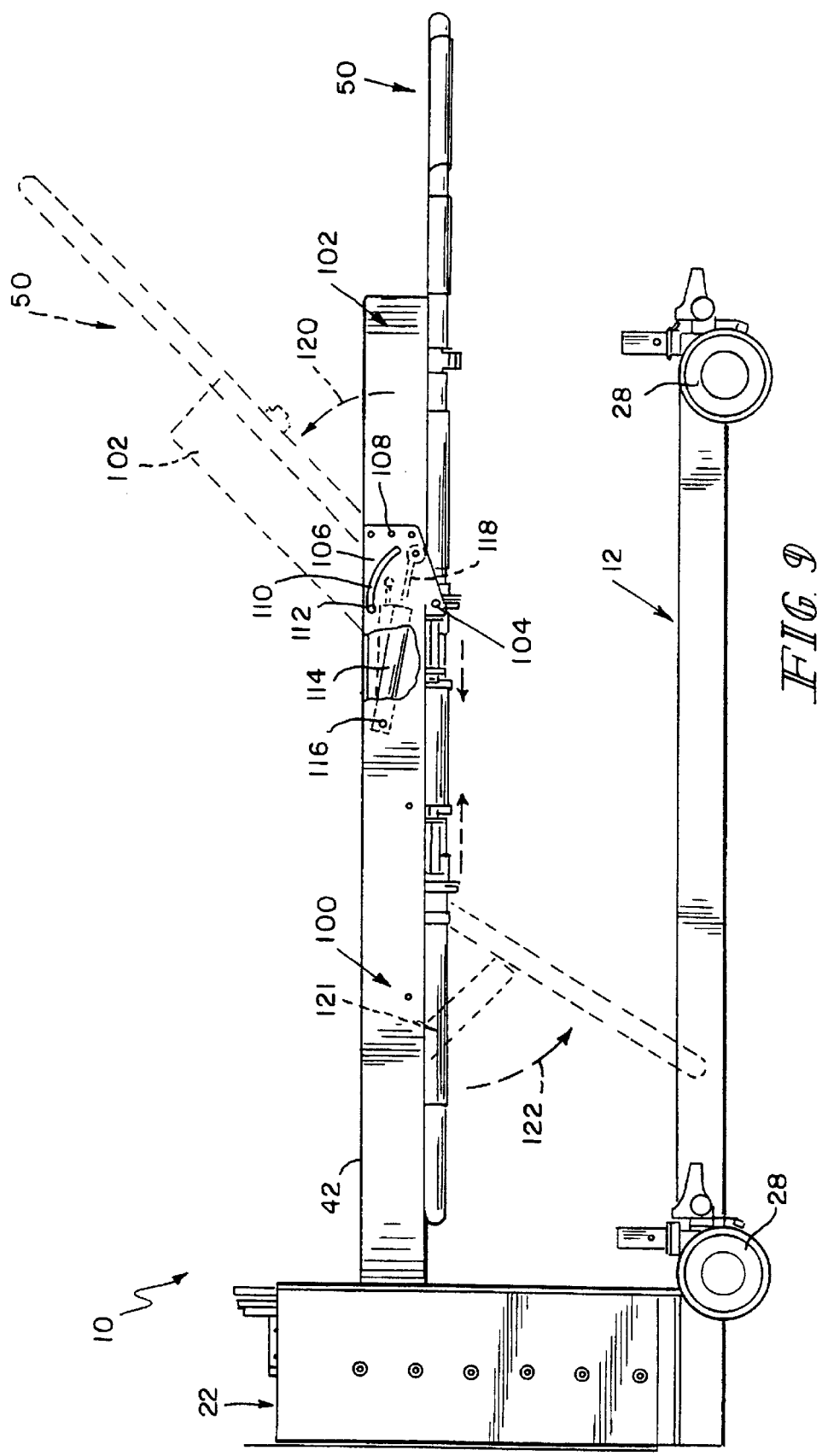
FIG. 9 is a side elevational view illustrating articulation of the first and second support arms and the patient support surface.

As best illustrated in FIGS. 1, 2 and 9, the support arms 42 and 44 each include foot end sections 100 and head end sections 102 which are pivotably coupled to foot end sections 100 by pivot connections 104. Plates 106 are rigidly coupled to head end sections 102 by fasteners 108. Plates 106 are formed to include arcuate slots 110 which slide over pins 112 coupled to foot end sections 100 of arms 42 and 44. Therefore, head end sections 102 can pivot upwardly relative to foot end sections 100 to elevate the head end of the bed.

A cylinder 114 is pivotably coupled to each foot end section 100 of arms 42 and 44 by a pivot connection 116 best shown in FIG. 9. Cylinders 114 include pistons 118 which are pivotably coupled to head end sections 102 of side arms 42 and 44. When the pistons 118 are in the extended position shown in FIG. 9, the head end sections 102 and foot end sections 104 of arms 42 and 44 are generally parallel. When piston 118 is retracted, head end sections 102 pivot upwardly as shown in FIG. 9 to elevate the head end of the bed 10 in the direction of arrow 120 of FIG. 8. An internal frame and drive mechanism 121 is provided to move the leg section patient support surface 50 downwardly in the direction of arrow 122, if desired.

Figure 11:
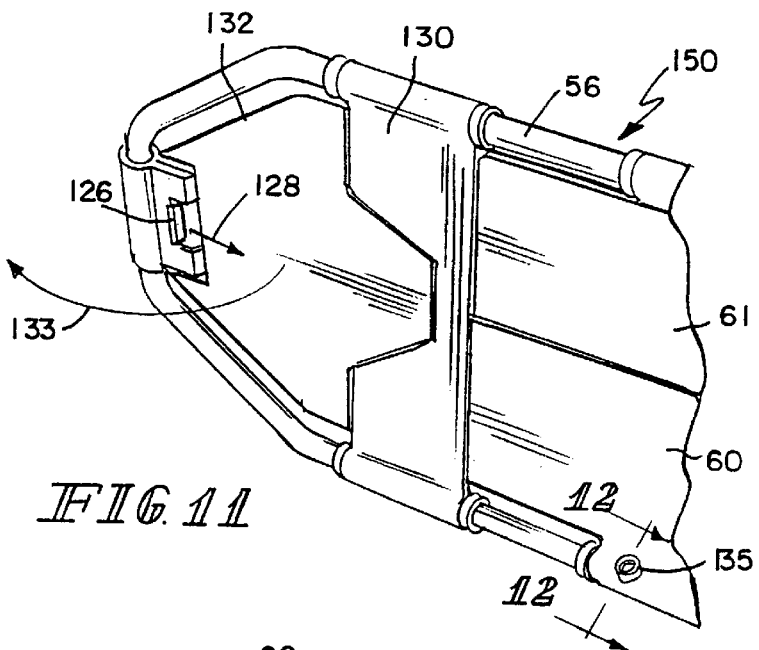
FIG. 11 is a perspective view of the patient support surface of FIG. 10 illustrating latch mechanisms for holding panels of the patient support surface in a generally planar orientation.
Figure 12:
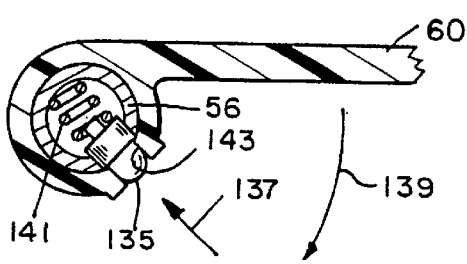
FIG. 12 is a sectional view taken along lines 12—12 of FIG. 11 illustrating details of one of the latch mechanisms.
Figure 13:
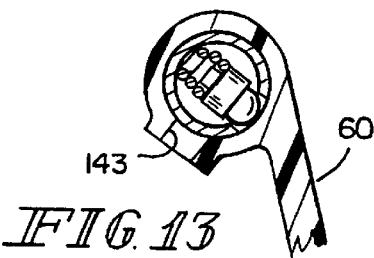
FIG. 13 is a sectional view of the latch mechanism of FIG. 12 which has been actuated to release the panel and permit pivotable movement of the panel relative to the outer frame of the patient support surface.

As discussed above, the panels 58–65 of patient support surface 50 are pivotable relative to the outer frame 56. FIGS. 11 and 12 illustrate another embodiment of a head support mechanism including a fixed member 130 extending between opposite sides of frame 56 and a pivotable head portion 132. Head portion 132 is pivotable outwardly relative to a head end of frame 56 when latch 126 is activated as illustrated by arrow 133. FIG. 11 illustrates a release plate 126 which must be pushed inwardly toward the center of the patient support surface 50 in the direction of arrow 128 in order to release the panel 131 for pivotable movement. This reduces the likelihood that the latch mechanisms 126 will be inadvertently actuated by a caregiver during transport. Another type of release mechanism is a push button release mechanism 135 illustrated in FIGS. 11–13. The push button 135 is located at an angle relative to frame member 56 so that push button 135 is not activated when the patient support surface 50 rests on the ground. Push button 135 is pressed in the direction of arrow 137 to release a panel 60 for pivotable movement in the direction of arrow 139 in FIG. 12. A spring 141 biases the push button 135 to the locking position of FIG. 12 when an aperture 143 formed in panel 60 is aligned with the push button 135. FIG. 13 illustrates the panel 60 in a downwardly pivoted position. It is understood that either type of latch mechanism 126, 135 may be used with any of the panels of the patient support surface 50.

FIGS. 14 and 15 illustrate a line management apparatus 144 configured to be coupled to a head end of the outer frame 56. Illustratively, the line management apparatus 144 includes a foam body 146 formed to include top notches 148 adjacent a top edge 149 and apertures 150 for routing IV lines or other hoses/lines 152, 154 to the patient as shown in FIG. 15. A clip 156 is coupled to body 146. Clip 156 is illustratively a C-shaped clip configured to be coupled frame 56.

Each of the panels 58–65 of patient support surface 50 is covered with a pressure reducing surface such as foam 158, etc., and a cover 160 as shown in FIG. 16. FIG. 17 illustrates an elastic material 162 such as Spandex which is filled with styrofoam beads 163 or other material. This elastic material 162 is illustratively placed within an outer cover 164 which has a controlled air leakage and which holds its shape for a predetermined amount of time. The outer cover 164 permits the inner elastic bag 162 of styrofoam beads 163 to be conformed to the shape of the patient. In one embodiment, the outer cover 164 or the inner bag 162 is be formed to include a heating element made from, for instance, a resistive heating element such as Gorix™ material. A controller (not shown) is coupled to the heating element. The heating material is used to warm the patient on the patient support surface 50. Various combinations of the bags 162 and 164 positioned over foam or contoured foam may be used on each section 58–65 of the patient support surface 50.

A movable transfer surface 170 is illustratively coupled to base 12 as shown in FIGS. 1 and 2. Surface 170 is lifted upwardly when the patient support surface 50 is loaded onto or removed from bed 10 by a suitable lifting mechanism 172 coupled between the surface 170 and base 12. Lifting mechanism 172 is any conventional lifting mechanism such as a scissors lift linkage, parallelogram linkage, etc. Surface 170 moves upwardly in the direction of arrow 174 in FIG. 2 and can support the patient support surface 50 if the latch mechanisms should fail. If desired, the surface 170 can remain in its upwardly lifted, elevated position below patient support surface 50, except for during rotation of the patient, when surface 170 must be lowered. As discussed above, the surface 170 may be used to open latches 81, 82 and 84.

Figure 18:
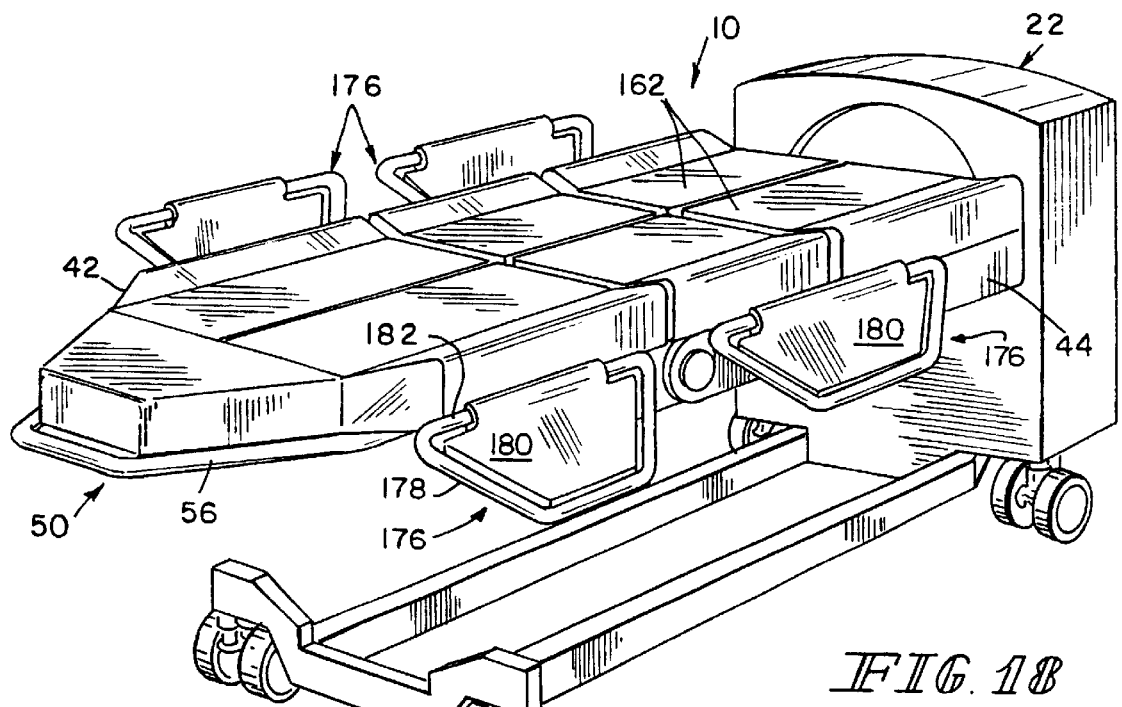
FIG. 18 is a perspective view of the proning bed of the present invention with side rails mounted to the first and second support arms.
Figure 19:
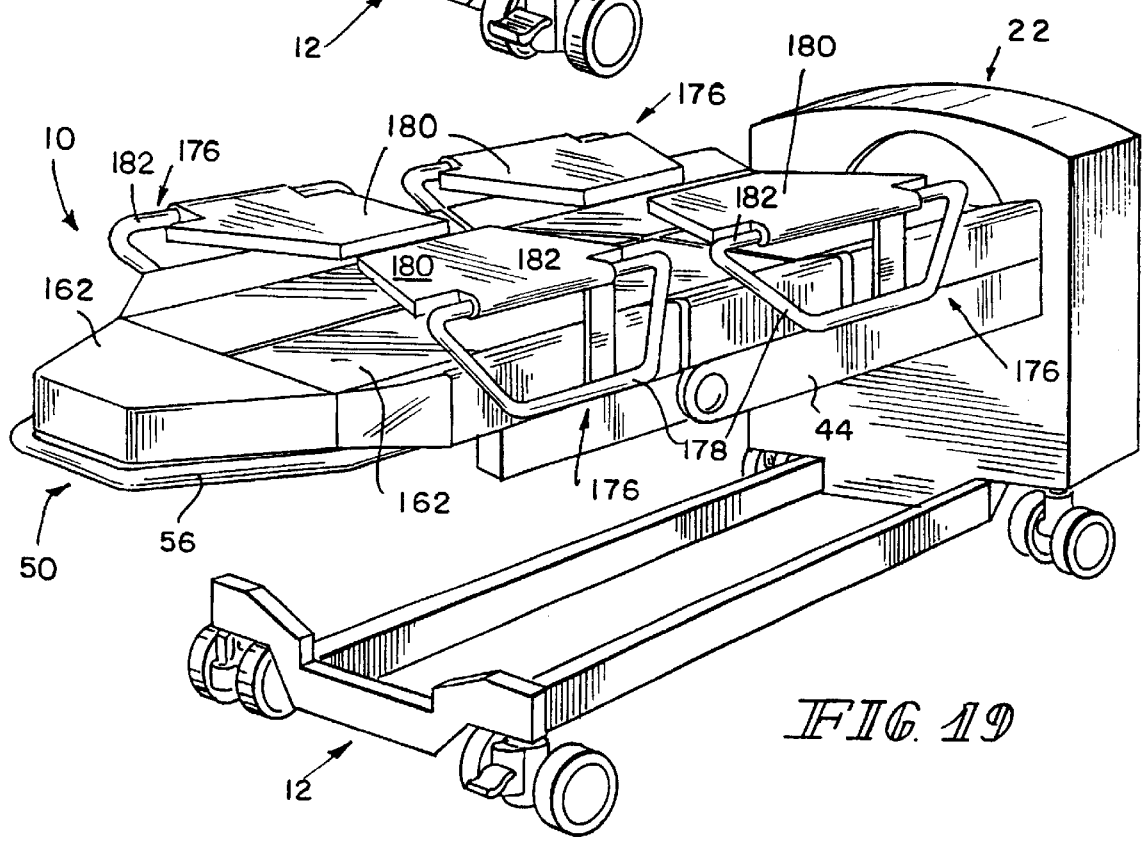
FIG. 19 is a perspective view of the bed of FIG. 18 illustrating portions of the side rails being positioned over the patient support surface to provide a proning support surface for the proning bed.

When it is desired to rotate the patient in order to move the patient to a prone position, a suitable proning surface is placed over the patient. The proning surface is coupled to side arms 42 and 44. FIGS. 18 and 19 illustrate one embodiment of the proning support surface. In this embodiment, outwardly clocking siderails 176 are pivotably coupled to support arms 42 and 44. The siderails 176 include an outer frame member 178 and an inner member 180 rotatably coupled to a top bar 182 of the frame member 178. The siderails 176 are movable to a lowered position illustrated by the siderails coupled to support arm 44 in FIG. 18. The siderails 176 are also movable to an elevated position illustrated by the other siderails 176 coupled to arm 42 in FIG. 18. After the siderails 176 are in the elevated position, center portions 180 are pivoted over a patient on the patient support surface 50 as shown in FIG. 19 to provide a prone support surface. A suitable surface for supporting the patient's head and body (not shown) is coupled to the sections 180 above the patient. Latches may be provided, if necessary, to secure the members 180 located on opposite sides of the bed 10 together for proning.

Although the invention has been described in detail with reference to a certain illustrated embodiments, variations and modifications exist within the scope and spirit of the invention as described and as defined in the following claims.

What is claimed is:

1. A bed apparatus comprising:
    a base;
    a support assembly coupled to the base, the support assembly including first and second support arms located above the base;
    a plurality of latch mechanisms coupled to the first and second support arms, the plurality of latch mechanisms each including a first latch portion and a second latch portion being configured to move with respect to the first latch portion; and a patient support surface configured to be coupled to the first and second support arms by the plurality of latch mechanisms, the patient support surface being removable from the first and second support arms to permit transfer of a patient to and from the bed on the patient support surface.

2. The apparatus of claim 1, wherein the support assembly includes a lifting mechanism coupled to the base to move the first and second support arms up and down relative to the base.

3. The apparatus of claim 1, wherein the base has a first end and a second end, the support assembly is coupled to the base adjacent the first end, and the support assembly including a rotatable drive mechanism coupled to the first and second support arms for rotating the first and second arms about a longitudinal axis.

4. The apparatus of claim 3, wherein the first and second support arms are cantilevered from the support assembly.

5. The apparatus of claim 3, further comprising a proning surface configured to be coupled to the first and second support arms, the proning surface being configured to support the patient in a prone position when the patient support assembly is rotated 180° about its longitudinal axis by the drive mechanism.

6. The apparatus of claim 5, further comprising a plurality of siderails coupled to the first and second support arms, the siderails each including a portion which is movable over the patient support surface to form a portion of the proning surface.

7. The apparatus of claim 1, wherein the patient support surface includes an outer frame configured to be coupled to the plurality of latch mechanisms to secure the patient support surface to the first and second support arms.

8. The apparatus of claim 7, wherein the patient support surface includes a plurality of panels coupled to the outer frame.

9. The apparatus of claim 8, wherein the panels include notched portions configured to define handles on the patient support surface.

10. The apparatus of claim 8, wherein the plurality of panels are pivotably coupled to the outer frame.

11. The apparatus of claim 1, wherein the patient support surface includes at least one hinge to permit articulation of the patient support surface, the hinge being selectively lockable to hold the patient support surface in a generally planar orientation.

12. The apparatus of claim 11, wherein the patient support surface includes at least one locking member configured to block pivotal movement of the hinge, the support assembly including an actuator for selectively releasing the locking member to permit articulation of the patient support surface.

13. The apparatus of claim 12, wherein a latching mechanism is configured to engage each locking member, the actuator being configured to move the latching mechanism relative to the first and second support arms to expose the hinge and permit articulation of the patient support surface.

14. The apparatus of claim 13, wherein the actuator includes a cylinder having a movable piston, a first end of the cylinder being coupled to one of the first and second support arms and a second end of the cylinder being coupled to the latch mechanism for moving the latch mechanism relative to the first and second support arms.

15. The apparatus of claim 12, wherein the locking member is a cylinder located over an outer frame of the patient support surface, the cylinder being movable from a first position to cover the hinge and a second position spaced apart from the hinge to permit articulation of the patient support surface.

16. The apparatus of claim 15, further comprising a spring coupled to the patient support surface to bias the cylinder the first position covering the hinge.

17. The apparatus of claim 1, wherein the first and second support arms each include a first portion coupled to the support assembly and a second portion pivotably coupled to the first portion to permit articulation of a head end of the patient support surface.

18. The apparatus of claim 17, further comprising a drive mechanism coupled to at least one of the first and second support arms and to the patient support surface, the drive mechanism being configured to articulate a leg section of the patient support surface relative to the first and second support arms.

19. The apparatus of claim 1, further comprising a transfer surface coupled to the base, the transfer surface being movable from a lowered position to an elevated position located adjacent the first and second support arms when the patient support surface is coupled to and removed from the first and second support arms.

20. The apparatus of claim 19, wherein the transfer surface is configured to engage a portion of the plurality of latch mechanisms as the transfer surface is moved to the elevated position to open the latch mechanisms for receiving the patient support surface.

21. A line management apparatus configured to be coupled to a patient support surface for routing medical lines and hoses, the apparatus comprising a body portion having a top edge, the body portion being formed to include a plurality of notches opening along the top edge to receive the lines and hoses, the bottom body portion also being formed to include a plurality of apertures located below the notches for receiving additional lines and hoses, and a coupler coupled to the body portion adjacent to the plurality of apertures, the coupler being configured to connect the body portion to the patient support surface.

22. The apparatus of claim 21, wherein the body portion is made from a foam material.

23. The apparatus of claim 21, wherein the coupler is a clip coupled to the body portion.

24. The apparatus of claim 23, wherein the clip is generally C-shaped.

25. A bed comprising:
a base having a first end and a second end;
a support assembly coupled to the base adjacent the first end, the support assembly including first and second support arms located above the base, and a rotatable drive mechanism coupled to the first and second support arms for rotating the first and second support arms about a longitudinal axis;
a plurality of latch mechanisms coupled to the first and second support arms; and
a patient support surface configured to be coupled to the first and second support arms by the plurality of latch mechanisms, the patient support surface being removable from the first and second support arms to permit transfer of a patient to and from the bed on the patient support surface.

26. The bed of claim 25, wherein the first and second support arms are cantilevered from the support assembly.

27. The bed of claim 25, further comprising a proning surface configured to be coupled to the first and second support arms, the proning surface being configured to support the patient in a prone position when the patient support assembly is rotated 180° about its longitudinal axis by the drive mechanism.

28. The bed of claim 27, further comprising a plurality of siderails coupled to the first and second support arms, the siderails each including a portion which is movable over the patient support surface to form a portion of the proning surface.

29. A bed comprising:
a base;
a support assembly coupled to the base, the support assembly including first and second support arms located above the base;
a plurality of latch mechanisms coupled to the first and second support arms;
a patient support surface configured to be coupled to the first and second support arms by the plurality of latch mechanisms, the patient support surface being removable from the first and second support arms to permit transfer of a patient to and from the bed on the patient support surface; and
wherein the patient support surface includes an outer frame and a plurality of panels coupled to the outer frame, the outer frame being configured to be coupled the plurality of latch mechanisms to secure the patient support surface to the first and second support arms.

30. The bed of claim 29, wherein the panels include notched portions configured to define handles on the patient support surface.

31. The bed of claim 29, wherein the plurality of panels are pivotably coupled to the outer frame.

32. A bed comprising:
a base;
a support assembly coupled to the base, the support assembly including first and second support arms located above the base;
a plurality of latch mechanisms coupled to the first and second support arms;
a patient support surface configured to be coupled to the first and second support arms by the plurality of latch mechanisms, the patient support surface being removable from the first and second support arms to permit transfer of a patient to and from the bed on the patient support surface;
the patient support surface including at least one hinge to permit articulation of the patient support surface, the hinge being selectively lockable to hold the patient support surface in a generally planar orientation;
at least one locking member configured to block pivotal movement of the hinge; and
the support assembly including an actuator for selectively releasing the locking member to permit articulation of the patient support surface.

33. The bed of claim 32, wherein a latching mechanism is configured to engage each locking member, the actuator being configured to move the latching mechanism relative to the first and second support arms to expose the hinge and permit articulation of the patient support surface.

34. The bed of claim 33, wherein the actuator includes a cylinder having a movable piston, a first end of the cylinder being coupled to one of the first and second support arms and a second end of the cylinder being coupled to the latch mechanism for moving the latch mechanism relative to the first and second support arms.

35. The bed of claim 32, wherein the locking member is a cylinder located over an outer frame of the patient support surface, the cylinder being movable from a first position to cover the hinge and a second position spaced apart from the hinge to permit articulation of the patient support surface.

36. The bed of claim 35, further comprising a spring coupled to the patient support surface to bias the cylinder the first position covering the hinge.

37. A bed comprising:
a base;
a support assembly coupled to the base, the support assembly including first and second support arms located above the base;
a plurality of latch mechanisms coupled to the first and second support arms;
a patient support surface configured to be coupled to the first and second support arms by the plurality of latch mechanisms, the patient support surface being removable from the first and second support arms to permit transfer of a patient to and from the bed on the patient support surface; and
wherein the first and second support arms each include a first portion coupled to the support assembly and a second portion pivotably coupled to the first portion to permit articulation of a head end of the patient support surface.

38. The bed of claim 37, further comprising a drive mechanism coupled to at least one of the first and second support arms and to the patient support surface, the drive mechanism being configured to articulate a leg section of the patient support surface relative to the first and second support arms.

39. A bed comprising:
a base;
a support assembly coupled to the base, the support assembly including first and second support arms located above the base;
a plurality of latch mechanisms coupled to the first and second support arms;
a patient support surface configured to be coupled to the first and second support arms by the plurality of latch mechanisms, the patient support surface being removable from the first and second support arms to permit transfer of a patient to and from the bed on the patient support surface;
a transfer surface coupled to the base, the transfer surface being movable from a lowered position to an elevated position located adjacent the first and second support arms when the patient support surface is coupled to and removed from the first and second support arms; and
wherein the transfer surface is configured to engage a portion of the plurality of latch mechanisms as the transfer surface is moved to the elevated position to open the latch mechanisms for receiving the patient support surface.

40. A bed comprising:
a base defining a longitudinal axis;
first and second arms located above the base and extending substantially parallel to the longitudinal axis;
a plurality of latch mechanisms spaced along the first and second arms, and
a patient support surface configured to be coupled to the first and second support arms by the plurality of latch mechanisms, the patient support surface being removable from the first and second support arms.

41. The bed of claim 40, wherein the plurality of latch mechanisms each include a first latch portion and a second latch portion configured to move relative to the first latch portion.

42. The bed of claim 40, further comprising a lifting mechanism coupled to the base and configured to move the first and second support arms up and down relative to the base.

43. The bed of claim 40, wherein the patient support surface includes an outer frame configured to be coupled to the plurality of latch mechanisms to secure the patient support surface to the first and second support arms.

44. A bed comprising:

a base;

first and second support members located above the base;

a patient support surface configured to be removably supported by the first and second support members; and means for latching the patient support surface to the first and second support members, the means for latching being movable between a latched position and an open position, wherein the means for latching, when in the latched position, prevents removal of the patient support surface supported by the first and second support members.

45. The bed of claim 44, wherein the means for latching comprises a first latch portion and a second latch portion configured to move relative to the first latch portion between the latched and open positions.

* * * * *